US012242011B2

(12) United States Patent
Omovie

(10) Patent No.: US 12,242,011 B2
(45) Date of Patent: Mar. 4, 2025

(54) METHOD FOR ESTIMATING WATER SATURATION IN GAS RESERVOIRS USING ACOUSTIC LOG P-WAVE AND S-WAVE VELOCITES

(71) Applicant: Goshey Energy Services LLC, Parker, CO (US)

(72) Inventor: Sheyore John Omovie, Parker, CO (US)

(73) Assignee: GOSHEY ENERGY SERVICES, LLC, Parker, CO (US)

(*) Notice: Subject to any disclaimer, the term of this patent is extended or adjusted under 35 U.S.C. 154(b) by 0 days.

(21) Appl. No.: 18/654,884

(22) Filed: May 3, 2024

(65) Prior Publication Data

US 2025/0044474 A1    Feb. 6, 2025

Related U.S. Application Data

(60) Provisional application No. 63/563,884, filed on Mar. 11, 2024, provisional application No. 63/530,494, filed on Aug. 3, 2023.

(51) Int. Cl.
*G01V 1/52* (2006.01)
*G01N 29/04* (2006.01)
*G01N 33/24* (2006.01)

(52) U.S. Cl.
CPC ............ *G01V 1/52* (2013.01); *G01N 29/043* (2013.01); *G01N 33/241* (2013.01); *G01N 33/246* (2013.01); *G01N 2291/02441* (2013.01); *G01N 2291/0422* (2013.01); *G01V 2200/16* (2013.01)

(58) Field of Classification Search
CPC .... G01V 1/52; G01V 2200/16; G01N 29/043; G01N 33/241; G01N 33/246; G01N 2291/02441; G01N 2291/0422
See application file for complete search history.

(56) References Cited

U.S. PATENT DOCUMENTS

| | | | |
|---|---|---|---|
| 11,914,091 B2* | 2/2024 | Fawad | G01V 1/306 |
| 2017/0293044 A1* | 10/2017 | Gilstrap | E21B 47/005 |
| 2022/0236438 A1* | 7/2022 | Fawad | G01V 1/50 |

FOREIGN PATENT DOCUMENTS

| | | | | |
|---|---|---|---|---|
| CN | 103257360 B | * | 5/2016 | |
| CN | 108508481 B | * | 11/2019 | G01V 1/28 |
| CN | 110658553 A | * | 1/2020 | G01V 1/307 |

* cited by examiner

*Primary Examiner* — Daniel Pihulic
(74) *Attorney, Agent, or Firm* — Sterne, Kessler, Goldstein & Fox P.L.L.C.

(57) ABSTRACT

The present application relates to new systems and methods of quantifying hydrocarbon saturation using measured acoustic logs. The methods and systems herein can accurately quantify the water saturation and hydrocarbon percentage in a low resistivity low contrast shaly sand reservoir where previous methods would indicate the reservoir was wet. In an embodiment, the disclosed system utilizes acoustic logging equipment or tools and techniques to transmit and/or record acoustic signals. Acoustic logging equipment operates by generating acoustic signals and detecting the acoustic signals after the acoustic signals pass through one or more geologic formations.

17 Claims, 9 Drawing Sheets

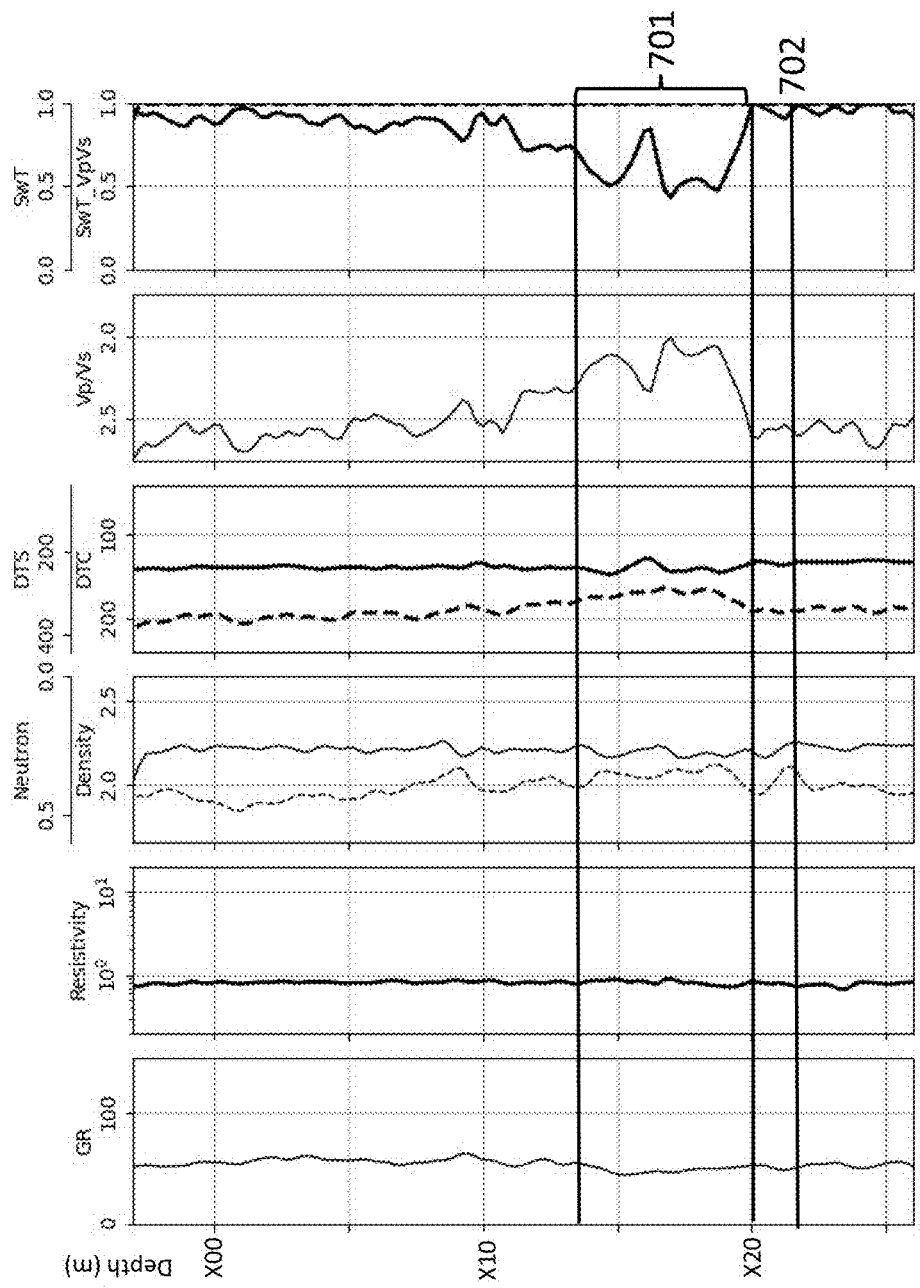

METHOD FOR ESTIMATING WATER SATURATION IN GAS RESERVOIRS USING ACOUSTIC LOG P-WAVE AND S-WAVE VELOCITES

CROSS REFERENCE TO RELATED APPLICATIONS

This application claims the benefit of priority under 35 U.S.C. § 119 to U.S. provisional application Ser. No. 63/530,494 filed Aug. 3, 2023. This application also claims the benefit of priority under 35 U.S.C. § 119 to U.S. provisional application Ser. No. 63/563,884 filed Mar. 11, 2024. The disclosure of the prior applications are considered part of and hereby incorporated by reference in the disclosure of this application.

FIELD OF DISCLOSURE

This disclosure relates generally to the field of well-log interpretation and petrophysical evaluation of subsurface formations. In particular, this disclosure recites a method for determining fluid saturations in subsurface formations that does not require the use of electrical resistivity measurements.

BACKGROUND

In the assessment of the potential of a hydrocarbon gas reservoir, the quantity of hydrocarbon is an important parameter. The hydrocarbon content determines whether a hydrocarbon reservoir contains a commercial quantity prior to reservoir development. Methods and systems have been developed in order to determine hydrocarbon content prior to the expensive and time-consuming process of drilling and extracting all the hydrocarbon in a formation. Prior systems have focused on determining the water content within a given underground space. Hydrocarbons occupy any space within a formation's pores not occupied by water.

In conventional reservoirs, the principal method for estimating water saturation is the Archie saturation model. In clean sand and sandstone reservoirs, Archie's saturation model has been proven effective assuming known brine or formation water resistivity. A major assumption of Archie's saturation model is that formation resistivity is primarily a function of the conductivity of the fluids filling pore space.

The assumption that formation resistivity is primarily a function of the fluids filling pore space is invalidated in formations with significant amounts of shale or other conductive minerals making up the rock matrix. In shaly sandstone and gas shale reservoirs with high brine conductivity (low brine resistivity), Archie's model can still be effective in determining water saturation. In situations with low brine salinity and high clay content, other saturation models have been developed but may not always outperform Archie's model.

In conventional reservoirs, nuclear magnetic resonance (NMR) logging is an alternative method for fluid typing that does not require the knowledge of formation resistivity (Rt) and brine resistivity (Rw). NMR logging allows for the quantification of fluid saturations, and with advances in NMR borehole technology, two-dimensional (2D) NMR imaging has become possible for this purpose.

There are limitations to the application of NMR logging tools for fluid characterization in unconventional reservoirs like shale gas and tight gas sandstone. These limitations arise from the lower porosity and permeability of these unconventional reservoirs, making it more challenging to obtain accurate measurements. Additionally, the lower frequency of NMR logging tools compared to laboratory-based NMR equipment can also impact the accuracy and resolution of the measurements. Another shortcoming of NMR logging tools is that they have a relatively shallow lateral depth of investigation compared to resistivity and acoustic logging tools for example. Thus, where there is significant mud invasion, the NMR logging tool may not be able to see beyond the flushed or invaded zone.

In addition to NMR logging and other conventional measurement methods, the features of an underground formation can be measured and characterized by a number of different parameters including by measuring the compressional waves and shear waves. There is a linear relationship between P-wave and S-wave velocity for water-bearing clastic reservoirs. When the fluid occupying the pore space in a reservoir is primarily gas or light oil, a formation's bulk modulus is significantly affected but the shear modulus stays relatively constant. This leads to a lower velocity ratio in gas or light oil siliciclastic reservoirs. This concept is often used in the seismic interpretation of conventional reservoirs for fluid identification.

Prior art examples focus on qualitatively determining the presence of hydrocarbons from the lower velocity ratio associated with hydrocarbon reservoirs. There is still a need to quantify fluid saturations in formations where conventional saturation models are not effective and that does not make the assumptions common to conventional saturation models.

Accordingly, the present application relates to new systems and methods of quantifying hydrocarbon saturation using measured acoustic logs. The improvement in technology and operation over prior methods and systems provides a significant increase in results. The methods and systems herein can accurately quantify the water saturation and hydrocarbon percentage in a low resistivity low contrast shaly sand reservoir where previous methods would indicate the reservoir was wet. Embodiments herein can accurately estimate water and hydrocarbon saturation over a wider range of subsurface conditions.

BRIEF DESCRIPTION OF THE DRAWINGS

FIG. 7a is a well log plot of a shaly sand reservoir where conventional saturation models are ineffective in quantifying water saturation.

FIG. 7b is a P-wave and S-wave velocity cross plot of indicated intervals in the well log plot of FIG. 7a.

DETAILED DESCRIPTION

The following description is presented to enable one of ordinary skill in the art to make and use this disclosure and is provided in the context of a patent application and its requirements. Various modifications to the embodiment will be readily apparent to those skilled in the art and the generic principles herein may be applied to other embodiments. Thus, the present disclosure is not intended to be limited to the embodiment shown but is to be accorded the widest scope consistent with the principles and features described herein.

Acoustic signals can propagate through formations as compressional and shear waves. Acoustic signals may be actively measured by sending out and recording. The velocities of compressional and shear acoustic waves depend on various formation parameters such as lithology type, compaction and cementation degree, overburden stress, porosity, and saturating fluid type. Generally, changes in these parameters cause proportional increases or decreases in both compressional and shear velocities, except when gas or light oil (hydrocarbon) is present as part or all of the pore-filling fluid. Introducing a small amount of hydrocarbons in pore spaces leads to a significant reduction in compressional velocity, especially when the hydrocarbon is gas, while increasing hydrocarbon saturation slightly increases shear velocity. An improvement over conventional methods is realized by measuring changes in these parameters and comparing the measurements to known quantities or theorized quantities.

In an embodiment, the disclosed system utilizes acoustic logging equipment or tools and techniques to transmit and/or record acoustic signals. Acoustic logging equipment operates by generating acoustic signals and detecting the acoustic signals after the acoustic signals pass through one or more geologic formations. For example, an acoustic signal may be generated and the time for the acoustic signal to be received at the generation point or at one or more spaced receivers may be recorded. Recording the travel time allows for the calculation of sound velocity through subsurface formations to characterize the subsurface formations. As described in embodiments herein an acoustic logging tool may be used to generate acoustic signals and record acoustic signals.

Figure 1:
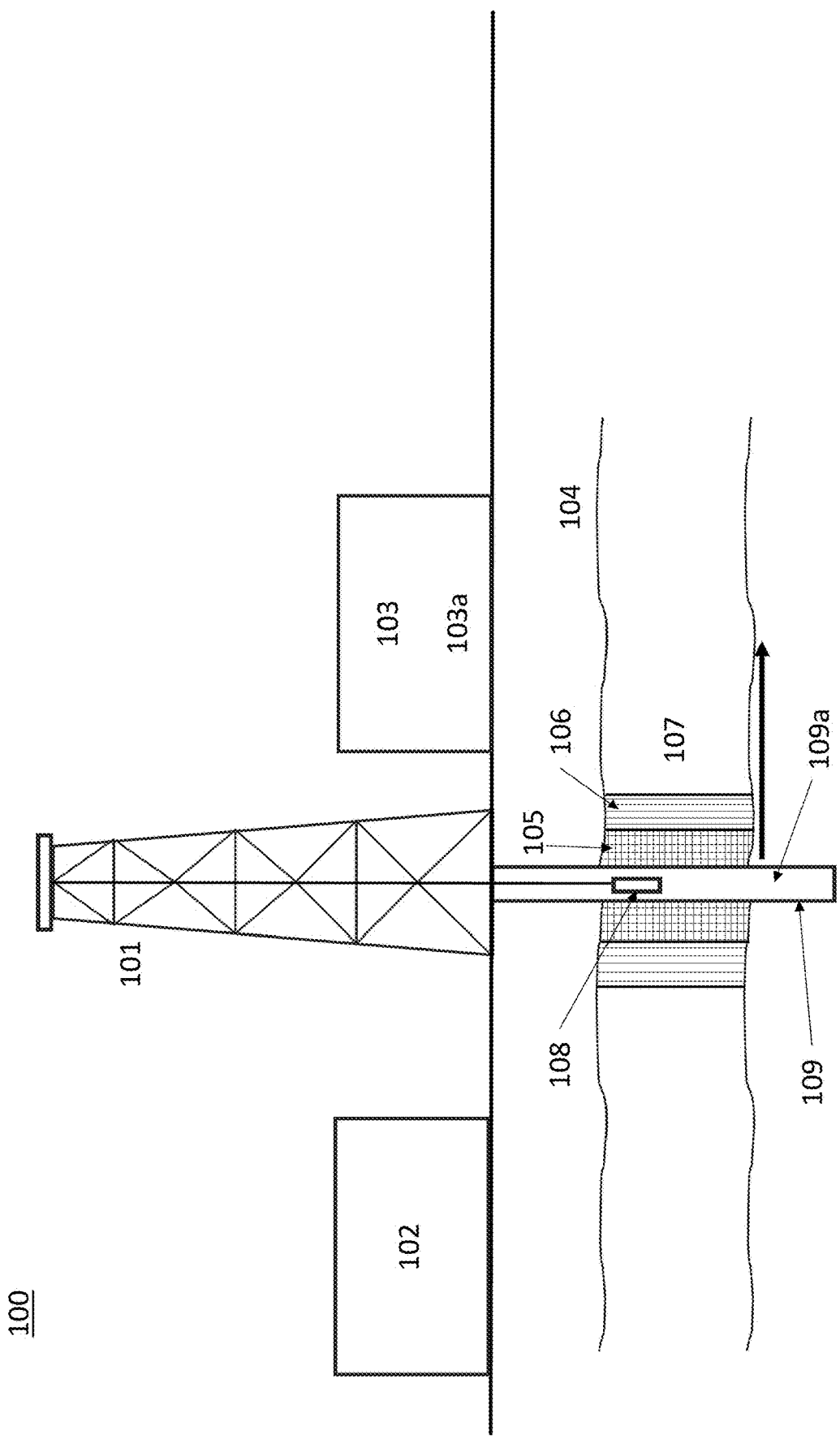
FIG. 1 is a diagram of an oil and gas well environment with instruments to measure, record, and transmit the subsurface formation properties of oil and gas reservoirs.
Figure 2:
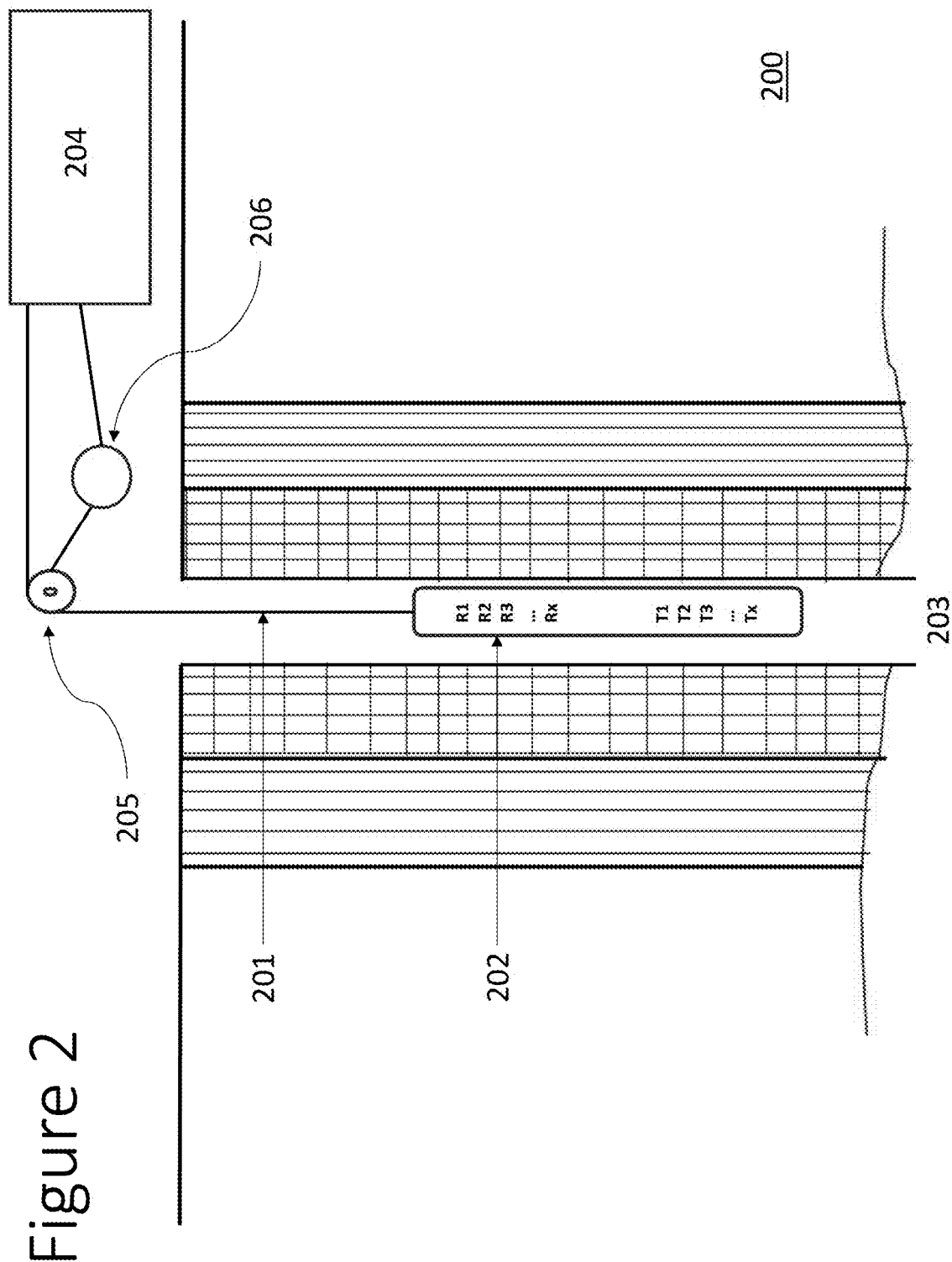
FIG. 2 is a diagram of an acoustic borehole logging system utilized for obtaining compressional wave velocity (Vp) and shear wave velocity (Vs) measurements within a subsurface formation.

The exemplary embodiments in FIGS. 1 and 2 depict how the wellbore environment is prepared and the acoustic data is recorded. A combination of hardware and software is used to process the acoustic data received into a hydrocarbon potential.

FIG. 1 depicts an oil and gas well environment. System 100 includes oil rig 101 which provides the infrastructure to create borehole 109. System 100 is operated by control system 102. Oil rig 101 and control system 102 operate to create borehole 109 into geologic formation 104. As part of the drilling process to create borehole 109 drilling fluid is flushed into borehole space 109a. A drilling fluid is forced into borehole 109 to remove drilled material. The drilling fluid penetrates geologic formation 104 proximal to borehole 109, displacing connate formation fluids. This penetration creates three subzones, invaded zone 105, transition zone 106, and uninvaded zone 107.

Invaded zone 105 is the space in which the drilling fluid has completely displaced connate fluid. Beyond invaded zone 105 is a zone of partial displacement of connate fluids referred to as transition zone 106. At lateral depths beyond the transition zone, connate fluids occupying the pore spaces of the formation are largely undisturbed by the drilling and flushing process. The undisturbed zone is uninvaded zone 107.

In an exemplary embodiment, measurement of the compressional and shear waves correspondents to uninvaded zone 107. However, the permeability or porosity of the geologic formation may cause a large invasion or transition zone. The increase in size may cause any acoustic measurement tools to record compressional and shear waves of the invaded or transition zones.

The zones are depicted as flat 2D rectangles with clear edges in FIG. 1. In practice the zones exist in 3D space and have an annular cross section. The distance from the center of the borehole radiating out horizontally and perpendicularly is referred to as the lateral depth. At each borehole depth there is a plane horizontal and perpendicular to the borehole depth direction. The lateral depth is any direction in this plane radiating outward from the center of the borehole. An example lateral depth is depicted in the 2D frame with the thick arrow in FIG. 1. Borehole depth is the direction along borehole 109. The edges of each zone may vary with borehole depth and along any lateral depth. Within the plane at any given borehole depth, each zone has a cross section. The cross section of any zone may vary from an ideal annulus depending on at least the precise composition of the geologic feature, the drilling fluid used, and porosity of the geologic rock. Any measurement tool as part of a method or system herein is lowered or moved into a wellbore to record information.

During operation, the acoustic measuring device is lowered through the wellbore. A motor for lowering the acoustic measuring device may be affixed to oil rig 101. Alternatively, a motor for lowering the acoustic measuring device may be located near oil rig 101. Movement is continuous and measurements are taken as the acoustic measuring devices move past different depths. In order to record information for a particular borehole depth an acoustic measuring device is positioned at or near the particular borehole depth. Bringing an acoustic measuring device to a particular depth may be referred to as horizontally adjacent to a particular underground feature, positioned horizontally adjacent a particular underground feature, lowered into the hydrocarbon reservoir, or moved into the hydrocarbon reservoir. Bringing an acoustic measuring device to a particular depth includes moving the acoustic measurement device past the particular depth at a speed. Alternatively, the acoustic measuring device may operate in a static position, move intermittently, or a combination thereof.

Additional non-depicted features may include a mud circulation system, drill pipes, and drill bits for drilling a wellbore. Logging system 103 may include well logging tools, surface and subsurface sensors, and instruments used to measure, record, and transmit the subsurface formation properties of an oil and gas reservoir.

In an exemplary embodiment, one or more acoustic logging tools 108 may be lowered or moved into borehole space 109a to the borehole depth of geologic formation 104. The one or more acoustic logging tools 108 may be positioned horizontally adjacent to the geologic formation 104. FIG. 1 is an exemplary depiction of positioned horizontally adjacent. In the alternative, an acoustic logging tool may be positioned above, below, within the same horizontal plane as the borehole depth of interest. Compressional and shear data may be recorded by one or more acoustic logging tools 108. The recorded data is transmitted from one or more acoustic logging tools 108 to logging system 103, control system 102, or a combination thereof. The recorded data is transmitted along a wire that suspends the acoustic logging tools 108, (acoustic logging tool 202 in FIG. 2). The wire depicted in FIG. 1 may be shielded, insulated, or otherwise coated to protect the signals from the wellbore environment. As is further described in other embodiments, the acoustic logging tools 108 may be lowered into borehole 109 with a motor.

In addition to one or more acoustic logging tools 108, additional well logging tools 103*a* may be included at or near the surface. Additional well logging tools 103*a* are connected to logging system 103 or control system 102 to transmit recorded data. The operation of logging system 103 is controlled by controlled system 102. FIG. 1 depicts the control system 102 and logging system 103 as separate. Control system 102 may have a display and user input. Logging system 103 may have a display and user input. In embodiments the control system 102 and logging system 103 may be implemented in the same component or device. Control system 102 and logging system may contain one or more processors connected to memory for recording received data and accessing instructions. The method steps may be expressed or stored as instructions in memory. By accessing the instructions, system 100 improves operation to make a more accurate and reliable assessment of water saturation and hydrocarbon potential of a geologic formation. Control system 102, logging system 103, or both may include controller 1900 in FIG. 8 as will be described in more detail below.

In some embodiments, an acoustic logging tool may be used for measuring compressional and shear data of a geologic formation in uninvaded zone 107. In some embodiments, other surface or subsurface logging tools that is capable of recording compressional and shear data may be used.

FIG. 2 is an acoustic borehole logging system utilized for obtaining compressional wave velocity (Vp) and shear wave velocity (Vs) measurements within a subsurface formation. The elements of FIG. 2 operate to measure subsurface formation characteristics to identify the hydrocarbon content of the formation in accordance with embodiments herein. System 200 is an idealized representation of lowering acoustic logging tool 202 by cable 201 into borehole 203. The operation of system 200 may be referred to as a wireline logging operation. Cable 201 extends from acoustic logging tool 202 over sheave or pulley 205 and terminates in logging system 204. Logging system 204 includes control hardware and software which drives motor 206. In turn motor 206 rotates sheave or pulley 205. By rotating sheave or pulley 205 counterclockwise the acoustic logging tool 202 is lowered into borehole 203. Clockwise rotation raises acoustic logging tool 202. Logging system 204 houses a portion of cable 201. Cable 201 may be shielded, insulated, or otherwise coated to protect transmitted measurements from the wellbore environment. By moving acoustic logging tool 202 to a subsurface position at or near an area of interest acoustic measurements can be recorded. Acoustic logging tool 202 may be in the same horizontal plane as a measured borehole depth, above a measured borehole depth, or below a measured borehole depth.

Acoustic logging tool 202 includes one or more acoustic transmitters. The acoustic transmitters are labelled as $T_1$, $T_2$, $T_3$ in FIG. 2. There may be any number of transmitters. Each transmitter emits a pulse of acoustic energy at a regular interval.

Acoustic logging tool 202 includes one or more acoustic receivers. For illustrative purposes, FIG. 2 depicts three acoustic receivers, which are labelled as R1, R2, and R3 in FIG. 2. Although three are shown, there may be any number of receivers. The acoustic receivers detect each of pulses emitted by the one or more acoustic transmitters and convert them into corresponding electrical signals. The corresponding electrical signals are transmitted by cable 201 to logging system 204. System 200 may be controlled by hardware and software included in logging system 204 or by a non-depicted control system. For example, system 200 may be controlled by control system 102 as shown in FIG. 1. The method steps may be expressed or stored as instructions in memory. By accessing the instructions, system 200 improves operation to make a more accurate and reliable assessment of water saturation and hydrocarbon potential of a geologic formation. Logging system 204 may include controller 1900 in FIG. 8 as will be described in more detail below.

FIGS. 1 and 2 are exemplary depictions of two operations for the lower acoustic equipment into a wellbore and recording information. FIG. 1 may bring acoustic logging tools 108 to the geologic formation with a motor and sheave or pulley attached to the oil rig or similar infrastructure that drilled the wellbore. Operation in FIG. 1 where a cable lowers the acoustic logging tools may be referred to as wireline logging operation. In some embodiments, acoustic logging tools 108 may be attached to the oilfield tools that drill the wellbore. As the wellbore is drilled and flushed measuring tools may be attached to and follow the drill bit into the wellbore. Operation in FIG. 1 where the measurement tools are attached to the drill bit or a pipe following the drill bit may be referred to as logging while drilling (LWD). In FIG. 1, the structure of acoustic logging tools 108 differs between LWD and wireline logging operations. In wireline logging, the acoustic logging tools are connected by cable and transmit signals to the surface by a wire. In LWD, acoustic logging tools 108 are connected to a drill bit or pipe and transmit measured data in real-time via mud pulse telemetry or other methods of transmitting data in real-time to logging system 103 as well as store recorded acoustic data until returned to the surface. System 200 in FIG. 2 makes similar measurements by removing the drilling equipment and using separate motor, sheave or pulley, and control system. Operation of system 200 in FIG. 2 may be referred to as a wireline logging operation. A person of ordinary skill, given the disclosure herein, would appreciate that FIG. 1 and FIG. 2 have structural features that may be the same or structural features in one may be used in the other. In some embodiments, features may be used in either or both. For example, structural features that are the same include acoustic logging tool 202, including acoustic receivers and acoustic transmitters, may be used as acoustic logging tools 108 in FIG. 1. For example, that may be the same and/or may be switched include logging system 204 may be the same as control system 102 in FIG. 1, logging system 103 in FIG. 1, or both. Furthermore, a person of ordinary skill, given the disclosure herein, would appreciate that wireline operation and logging while drilling are different modes of operation steps of both methods may be the same. For example, wireline operation and logging while drilling both require measuring a subsurface formation by generating and recording acoustic signals.

According to embodiments herein, the acoustic measuring equipment may be stationary when recording, or preferably in motion through a subsurface space. Furthermore, a single measurement may be taken at each borehole depth, or a repeated series of measurements may be taken at each borehole depth. In some embodiments, a trendline may be created from recorded measurements by an acoustic logging tool, one or more processors connected to an acoustic logging tool, or a combination of both. While a single measurement may provide a data point, a plurality of measurements are required to create a trendline.

Figure 3:
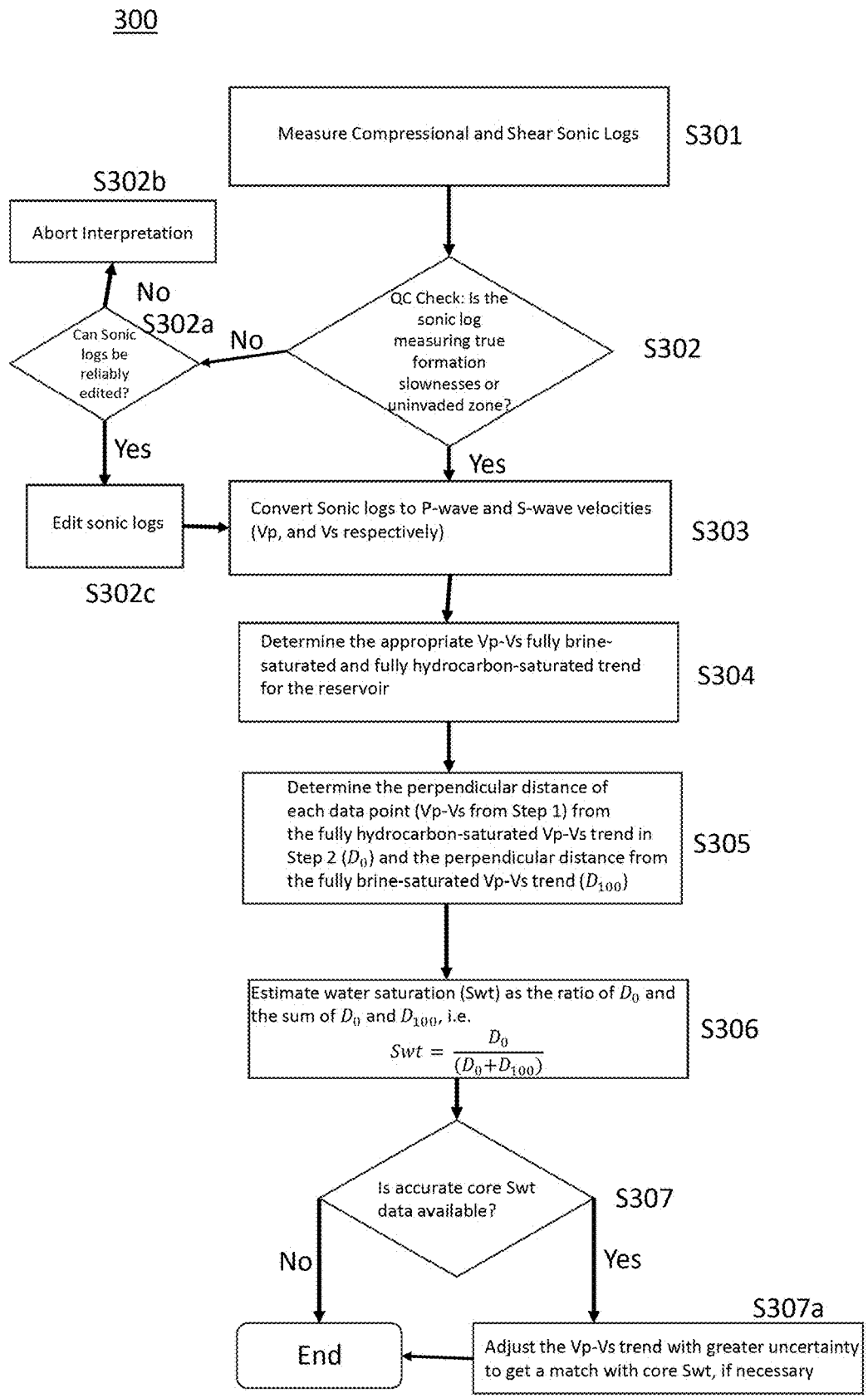
FIG. 3 is a flowchart for an embodiment of a system for determining the hydrocarbon potential of a subsurface rock formation.

FIG. 3 is a flowchart for an embodiment of a system for determining the hydrocarbon potential of a subsurface geologic formation. Method 300 includes steps for finding water saturation of a hydrocarbon reservoir in order to estimate the hydrocarbon potential. The steps in FIG. 3 are performed by an acoustic logging tool, one or more processors connected to an acoustic logging tool, or a combination of both. Exemplary hardware embodiments for performing the steps in FIG. 3 include FIG. 1 acoustic logging tool 108, control system 102, and logging system 103 and FIG. 2 acoustic logging tool 202 and logging system 204. At S301, an acoustic logging tool measures compressional and shear waves for a geologic formation suspected to contain hydrocarbons. The measurement tool records the compressional acoustic log (DTC) and shear acoustic log (v). When the fluid occupying the pore space in a formation is primarily gas or light oil, the formation's bulk modulus is significantly affected but the shear modulus stays relatively constant. Replacing some of the water within the pore spaces of the reservoir with hydrocarbons causes a significant decrease in P-wave velocity (compressional wave velocity), especially when the hydrocarbon is gas, with only a slight increase in S-wave velocity (shear wave velocity), leading to the observed lower Vp/Vs in hydrocarbon-bearing intervals.

According to embodiments herein, further drilling and hydrocarbon transport equipment may be provided. Equipment may include one or more pipes, one or more pumps, and control systems to control further drilling and transportation. Any equipment needed to further drill and transport hydrocarbons to the surface may be installed after acoustic logging tools have completed measurements. After the measurement and determination of a water and/or hydrocarbon saturation based on systems and methods included herein. The system may display an indication to extract hydrocarbons from the an underground formation if a sufficient amount of hydrocarbons are detected. The system may cause extraction of one or more hydrocarbons from the hydrocarbon reservoir. By more accurately characterizing the amount of hydrocarbons in a hydrocarbon reservoir, prior to extraction, a system may be able to make a more economical extraction decision. For example, with the embodiment depicted in FIG. 2, further hydrocarbon extraction equipment may be brought to the wellbore for further drilling and extraction. For example, with the embodiment depicted in FIG. 1, the onsite oil rig 101 and other equipment may be used for further drilling and extraction, or further hydrocarbon extraction equipment may be brought to the wellbore for further drilling and extraction. Alternatively, a new borehole may be drilled to access the hydrocarbon reservoir. One or more pipes may be inserted into the hydrocarbon reservoir to transport hydrocarbons to the surface.

Method 300 includes optional steps S302 and S302a-c. In S302 a quality check may be performed on the data by an acoustic logging tool, such as acoustic logging tool 202, one or more processors connected to an acoustic logging tool, or a combination of both. In S302, measured data is compared to known data for hydrocarbon reservoirs with similar geologic formations or from an offset well by an acoustic logging tool, one or more processors connected to an acoustic logging tool, or a combination of both. Measurements have been impacted by washouts or the measurements may be focused on the transition or invaded zones.

In S303 Equations 1 and 2 use measured values from S301 or as corrected in optional steps S302 and S302a-c, and convert the measured values into a shear velocity (Vs) and a compressional velocity (Vp).

$$Vp = 304.8009/DTC \quad \text{Equation 1}$$

$$Vs = 304.8009/DTS \quad \text{Equation 2}$$

S303 is performed by an acoustic logging tool, one or more processors connected to an acoustic logging tool, or a combination of both.

In S304, baseline trendlines are created by an acoustic logging tool, one or more processors connected to an acoustic logging tool, or a combination of both for comparison to the measured values. The amount of water that exists in a given volume is 0% to 100%. 0% water is fully dry or fully hydrocarbon. The 100% dry/hydrocarbon baseline is referred to as fully dry trend or fully hydrocarbon saturated trend. 100% water or brine is fully brine saturated. The 100% water/brine baseline is referred to as fully brine trend or fully brine saturated trend. First the Vs and Vp need to be determined for each of the fully dry trend and fully brine trend. Estimates or previously measured data may be used. By using theoretical or empirical data that is closely matched to the geologic formation of interest a more accurate final result (i.e., water saturation and hydrocarbon potential) may be determined. For example, a processor may calibrate the fully brine saturated trend to theoretical or empirical data.

For example, a reservoir that is fully brine with similar geologic characteristics near hydrocarbon reservoir interest may be used. An interval that is known to be fully brine saturated may be measured by an acoustic logging tool, one or more processors connected to an acoustic logging tool, or a combination of both and used as the fully brine baseline. A fully hydrocarbon-saturated trend may be obtained from the fully brine trend by means of fluid substitution. An empirical trend may also be used in the absence of a fully brine interval in a subsurface reservoir. For example, for the fully brine baseline Equations 3 and 4 may be used to estimate a trendline. Equations 5 and 6 are empirical fully dry or fully gas-saturated estimates for Vp and Vs from which a fully dry trendline can be determined.

$$V_{s\_100} = 0.7697 * V_{p\_100} - 0.8673 \text{ km/s} \quad \text{Equation 3}$$

$$V_{s\_100} = 0.527 * V_{p\_100} - 0.8673 \text{ km/s} \quad \text{Equation 4}$$

$$V_{p\_0} = 5.41 - 6.35 * \phi - 2.87 * C \quad \text{Equation 5}$$

$$V_{s\_0} = 3.57 - 4.57 * \phi - 1.83 * C \quad \text{Equation 6}$$

where C is clay volume and φ is total porosity. Equations 3-6 may be used by an acoustic logging tool, one or more processors connected to an acoustic logging tool, or a combination of both to calibrate a fully brine saturated trendline. The calibration may increase the accuracy of any water saturation or hydrocarbon saturation determinations.

Equations 7 and 8 are used by an acoustic logging tool, one or more processors connected to an acoustic logging tool, or a combination of both to create the fully hydrocarbon-saturated and fully brine trendlines respectively.

$$a_0 * x + b_0 * y + c_0 = 0 \quad \text{Equation 7}$$

where x and y are the P-wave and S-wave velocities respectively, $a_0$ is the coefficient of Vp, $b_0$ is the coefficient of Vs, and $c_0$ is the intercept for the fully dry trend $$a_{100}*x + b_{100}*y + c_{100} = 0 \quad \text{Equation 8}$$

where x and y are the P-wave and S-wave velocities respectively, $a_{100}$ is the coefficient of Vp, $b_{100}$ is the coefficient of Vs, and $c_{100}$ is the intercept for the fully brine trend.

In alternative embodiments, the coefficients may comprise other values. For example, $a_0$ and $a_{100}$ may be a coefficient of the bulk modulus (KB), $a_0$ and $a_{100}$ a coefficient of $V_p/V_s$, $b_0$ and $b_{100}$ may be a coefficient of DTS, $b_0$ and $b_{100}$ may be a coefficient of DTC, or a combination thereof.

Figure 5:
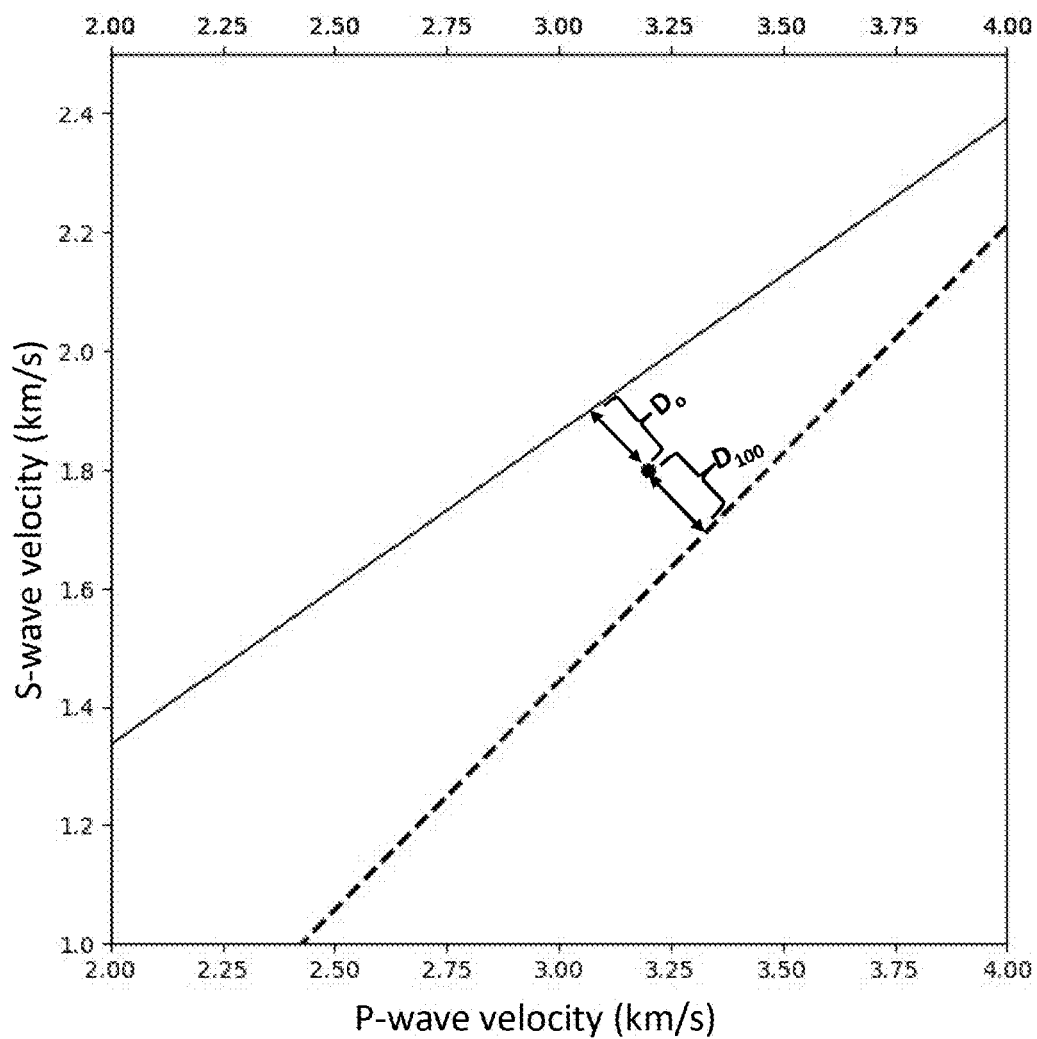
FIG. 5 is a diagram of an embodiment of an example of comparing the P-wave velocity and S-wave velocity to determine water saturation.

In S305, the perpendicular distance of the compressional wave velocity and shear wave velocity is determined by an acoustic logging tool, one or more processors connected to an acoustic logging tool, or a combination of both from the fully brine and fully hydrocarbon baseline trends. FIG. 5 is an exemplary demonstration of S305. The solid line represents the fully hydrocarbon-saturated Vp-Vs trend. The black dashed line is the 100% brine-saturated Vp-Vs regression trend. Equations 9 and 10 are used by an acoustic logging tool, one or more processors connected to an acoustic logging tool, or a combination of both to determine the perpendicular distance.

$$D_0 = \frac{|a_0 x + b_0 y + c_0|}{\sqrt{a_0^2 + b_0^2}} \quad \text{Equation 9}$$

where $D_0$ is the distance of a data point from the fully hydrocarbon trend.

$$D_{100} = \frac{|a_{100} x + b_{100} y + c_{100}|}{\sqrt{a_{100}^2 + b_{100}^2}} \quad \text{Equation 10}$$

where $D_{100}$ is the distance of a data point from the fully brine trend. Any value above or below a trendline would be set to 0% or 100% respectively.

In S306, water saturation is determined by an acoustic logging tool, one or more processors connected to an acoustic logging tool, or a combination of both based on the distance between the trendlines determined in S305. The percentage of water saturation at a given borehole depth for a Vs Vp data point is determined by an acoustic logging tool, one or more processors connected to an acoustic logging tool, or a combination of both with Equation 11.

$$Swt = D_0/(D_0 + D_{100}) \text{ where } Swt \text{ is water saturation percentage.} \quad \text{Equation 11}$$

Equation 11 may be substituted with Equations 9 and 10 to give Equation 12.

$$Swt = \frac{\frac{|a_0 x + b_0 y + c_0|}{\sqrt{a_0^2 + b_0^2}}}{\frac{|a_{100} x + b_{100} y + c_{100}|}{\sqrt{a_{100}^2 + b_{100}^2}} + \frac{|a_0 x + b_0 y + c_0|}{\sqrt{a_0^2 + b_0^2}}} \quad \text{Equation 12}$$

Further substitutions or rearrangement of the terms is envisioned.

S305, S306, or a subset of either may be referred to as determining a deviation. By determining the deviation between upper and lower baseline trends a user can determine where a sample of interest is relative to the baselines. This principle is demonstrated by the performing exemplary steps S305 and S306. S305 and S306, including determining a deviation, performed by an acoustic logging tool, one or more processors connected to an acoustic logging tool, or a combination of both. Exemplary hardware embodiments for performing S305 and S306 including determining a deviation, include FIG. 1 acoustic logging tool 108, control system 102, and logging system 103 and FIG. 2 acoustic logging tool 202 and logging system 204.

S307 and S307a are optional steps if additional data is available. If core water saturation is available the water saturations at various depths can be fit to these measured amounts. Fitting data to previously known data to improve the accuracy of current measurements may be performed by an acoustic logging tool, one or more processors connected to an acoustic logging tool, or a combination of both. Where core water saturation data is available, the trend with the most uncertainty (usually the fully hydrocarbon-saturated trend) may be adjusted slightly to get a match with the core data, if necessary. Core water saturation is taken from one or more core samples removed from a geologic formation. A drill bit is used to remove a cylindrical section of an underground formation. The cylindrical section is a core sample. Water saturation may be accurately measured from the cylindrical sample. A processor connected to one or more measurement tools may determine the water content of the core sample. The water content determined by the processor may be fed to an acoustic logging tool, one or more processors connected to an acoustic logging tool, or a combination of both. Water content from an exhumed core sample may be fed to the acoustic logging tool or processors connected to an acoustic logging tool during the during a recording operation or may be used by a processor to adjust the results at some time after recording has been completed. For example, core analysis may take a month or more and the determined water content is used by a processor to adjust the data at that time.

The water saturation is given by Equation 11 or Equation 12. The hydrocarbon presence is the percent volume not occupied by brine/water. To convert from water saturation to hydrocarbon saturation Equation 13 is used.

$$Sh = 1 - Swt \quad \text{Equation 13}$$

where Sh is hydrocarbon saturation.

Figure 4:
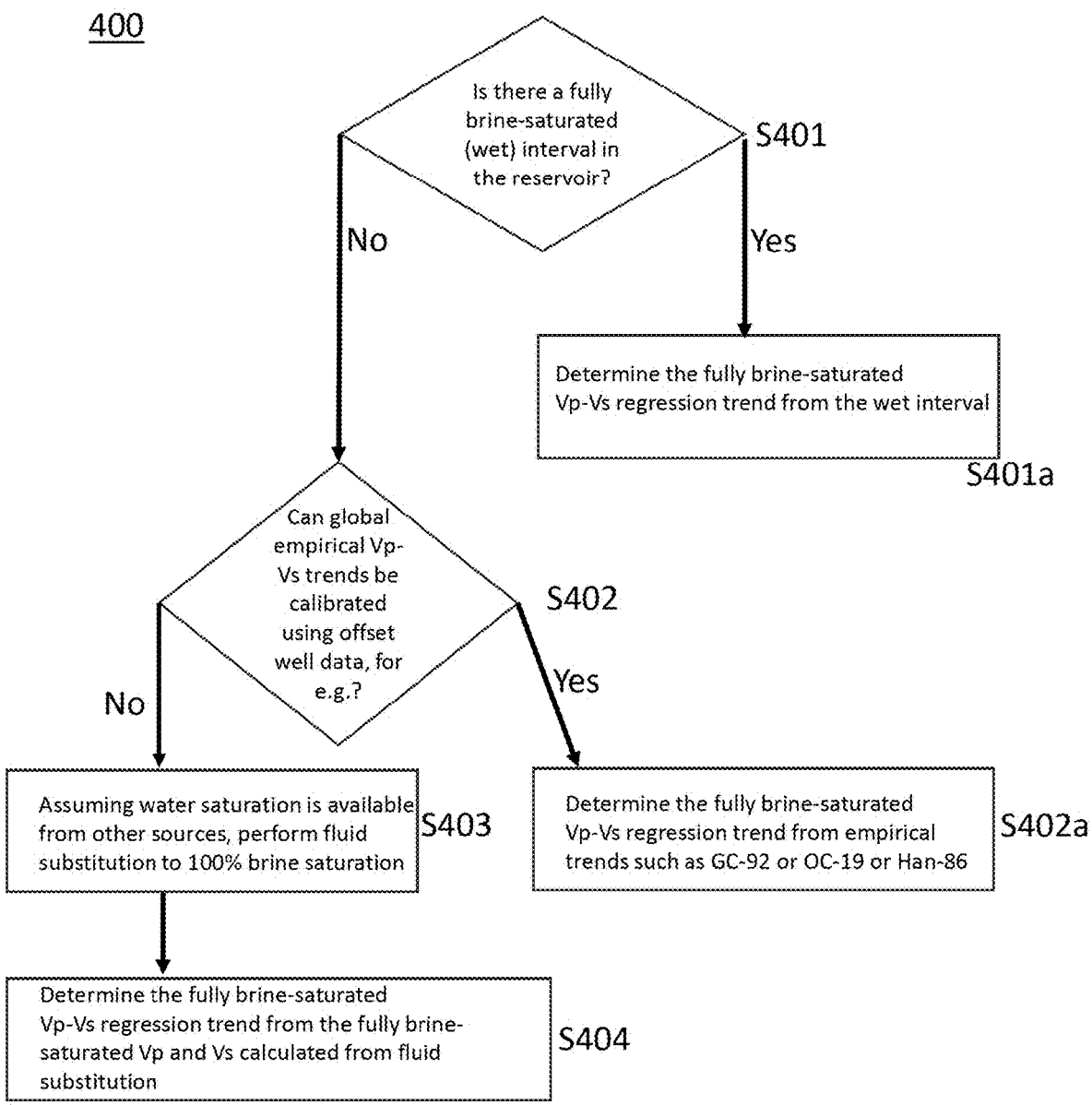
FIG. 4 is a flowchart of an embodiment of a system for determining the water-bearing or fully brine-saturated Vp-Vs trendline in order to determine the hydrocarbon potential of subsurface formation reservoirs.

FIG. 4 is a flowchart of an embodiment of a system for determining a fully brine trendline for determining a hydrocarbon potential of a subsurface reservoir. In order to determine the water saturation percentage trendlines for the upper and lower extremes are determined for a geologic formation of interest. In order to determine a trendline different methods may be employed depending on the composition of the geologic formation. The steps in FIG. 4 are performed by an acoustic logging tool, one or more processors connected to an acoustic logging tool, or a combination of both. Exemplary hardware embodiments for performing the steps in FIG. 4 include FIG. 1 acoustic logging tool 108, control system 102, and logging system 103 and FIG. 2 acoustic logging tool 202 and logging system 204.

Method 400 is an exemplary process for determining the fully brine trendline by an acoustic logging tool, one or more processors connected to an acoustic logging tool, or a combination of both. In S401 an acoustic logging tool, one or more processors connected to an acoustic logging tool, or a combination of both determine if there is a fully brine interval in the reservoir. An interval is a space or volume within a geologic formation. In S401 the interval, may, if present, have the compressional and shear waves measured by an acoustic logging tool, one or more processors connected to an acoustic logging tool, or a combination of both which gives the trendline for the fully brine trendline. Measuring the interval and determining a trendline is step S401a.

In S402, a fully brine interval is not available. A further determination of the characteristics of the geologic formation is needed. If offset well data is available then Equations 3-6 may be used in step 402a by an acoustic logging tool, one or more processors connected to an acoustic logging tool, or a combination of both.

If offset well data is not available then fluid substitution to 100% brine saturation is needed. S403 and S404 include fluid substitution and determining the trendline respectively. Methods known in the art may be used for fluid substitution. Fluid substitution may be performed by an acoustic logging tool, one or more processors connected to an acoustic logging tool, or a combination of both.

Figure 6:
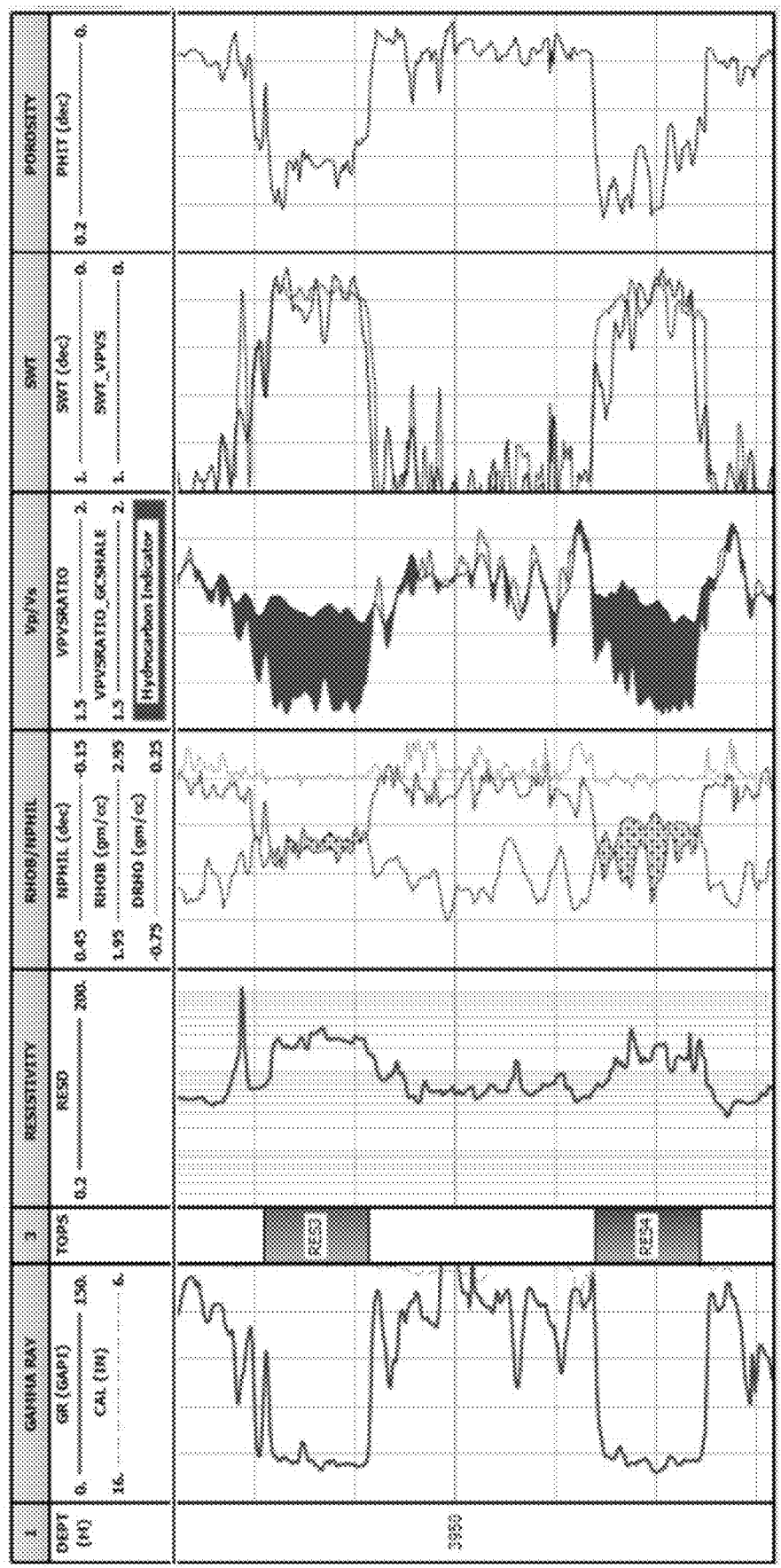
FIG. 6 is a well-log plot of data of a reservoir used with embodiments described herein.

FIG. 6 is an exemplary graphical depiction of hydrocarbon potential in a geologic formation. Column 6 of FIG. 6 is labeled Vp/Vs. Column 6 provides a visual demonstration of the hydrocarbon potential based on embodiments herein. In Column 6 two lines form an envelope with a dark shaded region defining the interior of the envelope. The first line is the velocity ratio computed from measured compressional and shear sonic logs. The second line is the velocity ratio estimated from the fully brine trendline assuming the reservoir is fully brine saturated. The separation between both lines—the dark shading—is an indication of the presence of hydrocarbons in the reservoir. The thicker the dark portion of the envelope the greater proportion of hydrocarbons are indicated as present at the corresponding depth.

Column 7 of FIG. 6 is labeled SWT. Column 7 provides a visual demonstration of the water saturation of the geologic formation based on embodiments herein. Column 7 is read left to right from 100% to 0% water saturation. A visual inspection reveals that the highest water saturation regions (around 3950 meters see Column 1) corresponds to the thinnest envelope in Column 6. Column 4 is the measured resistivity used in conventional saturation model to also estimate hydrocarbon potential in a geologic formation. Columns 2 and 5 are used to determine other formation properties such as lithology and porosity.

Figure 7B:
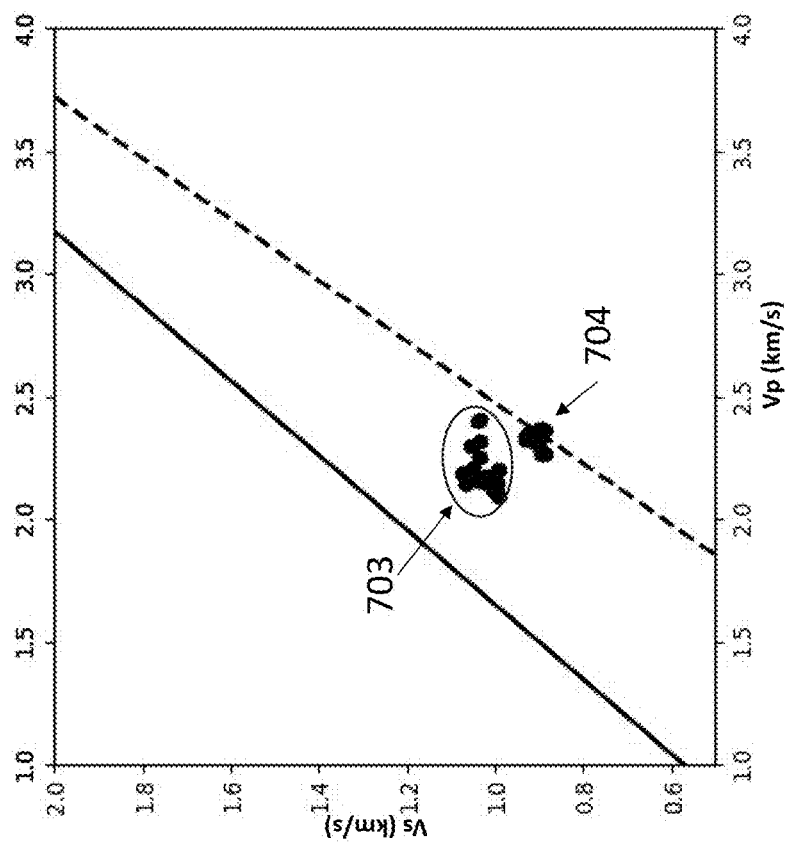

The methods and systems in FIGS. 1-4 were applied to a data set taken from a shaly sand reservoir. The outcome is presented in is presented in FIG. 7a along with data measured and processed using conventional techniques. FIG. 7a is a well log plot. FIG. 7b is a graphical depiction of applying some of the steps of FIGS. 3 and 4 to the data set presented in FIG. 7a. A brief description of some of the steps used to create FIGS. 7a and 7b. First compressional and shear data are recorded (S301) and Vp and Vs are computed from compressional and shear sonic log data (S303). Next, the fully brine saturated trendline is determined for the reservoir (S304). Turning to FIG. 4 a processor detects the presence of a water bearing interval and determines it is not a fully water bearing interval (S401). The processor relies on empirical data to calculate a fully brine saturated trendline (S402) and (S402a). Returning to FIG. 3, given the determined fully brine saturated trendline fluid substitution to 100% hydrocarbon saturation is performed by the processor to determine the fully hydrocarbon saturated trendline (S304). The processor determines the perpendicular distance of each data point from the brine-saturated and hydrocarbon-saturated trendlines (S305). FIG. 7b is a visual depiction of S305. The processor determines water saturation (S306) and hydrocarbon saturation. The processor plots the data and provides a display which is depicted in FIG. 7a. FIG. 7a Column 1 is the Gamma Ray log. The Gamma Ray log may be used for identifying lithology. FIG. 7a Column 2 is the resistivity log. The resistivity log is the primary method used in quantifying water saturation in conventional saturation models. FIG. 7a Column 3 is the neutron porosity. The neutron log is the dashed curve in Column 3. The bulk density is the dashed line in Column 3. Bulk density and neutron porosity are both used to determine porosity—the percentage of pore space within the reservoir or formation. FIG. 7a Column 4 is DTS and DTC. As in the for the methods and systems in FIGS. 1-4 a measurement tool records the DTC and DTS. DTC is the solid line in Column 4. DTS is the dashed line in column 4. The velocity ratio (Vp/Vs) is in Column 5. The water saturation percentage is in Column 6.

In FIG. 7a the vertical axis represents borehole depth. The columns are plotted against the borehole depth. The lower line of 701 in FIG. 7a represents a horizon below which the reservoir is 100% water-bearing. Above line 702, there exist in the pore spaces both hydrocarbons and water or brine. The embodiments herein provide systems and methods for differentiating between the hydrocarbons and water or brine in the pore spaces. Prior methods indicate the formation is 100% water saturated. This depicted by a vertical dashed line on the right side of Column 6. However, bracketed section 701 is a known gas reservoir. For example, the Archie method which relies in part on changes in formation resistivity misses the gas interval in bracketed section 701. Embodiments included herein improve the ability of a user to accurately determine hydrocarbon intervals where prior models fall short.

FIG. 7b is an example Vp versus Vs cross plot with trendlines and data taken from FIG. 7a. Datapoints 704 correspond to the data below line 702. Datapoints 703 correspond to the data in bracketed section 701. The angled dashed line in FIG. 7b represents the fully brine-saturated trendline. Datapoints 704 clustered at the dashed line indicate the formation at the corresponding depths has pore spaces filled with water or brine only. The angled solid line in FIG. 7b represents the fully hydrocarbon trendline. Datapoints 703, included within the circle, are clustered in a space between the fully hydrocarbon trendline and the fully brine-saturated trendline. Datapoints 703 indicate that the pore spaces at the corresponding depth are part water or brine and part hydrocarbon. Datapoints 703 indicate what prior methods missed.

Method 400 provides steps are performed by an acoustic logging tool, one or more processors connected to an acoustic logging tool, or a combination of both to determine the fully brine interval given various formation conditions. An example application is provided for the formation in the shaly sand reservoir which provided data for FIGS. 7a and 7b. The shaly sand reservoir has a fully brine saturated interval. In this example, following the flowchart in FIGS. 4 S401 and S401a are carried out. In the absence of a water-bearing interval within a reservoir, the appropriate trends could be determined from the flow chart in FIG. 4. After determining the fully brine trend, the fully hydrocarbon saturated trend may be determined using Gassmann or Biot fluid substitution.

In an embodiment, the embodiments in FIGS. 1-4 may be used to determine that a subsurface formation may not include any viable quantity of hydrocarbons. In a negative information scenario, similar steps are performed in order to characterize the subsurface formation. A water bearing interval may be measured by an acoustic logging tool, one or more processors connected to an acoustic logging tool, or a combination of both or an empirical comparison may be made. However, a hydrocarbon bearing interval would not be measured since the subsurface formation is devoid of a viable quantity of hydrocarbons. The deviation from the brine and hydrocarbon trendlines is an edge case. The recorded compressional and shear waves would give velocities that are at or near the fully brine-saturated trendline. A user would be interested in obtaining knowledge that a subsurface lacks a viable quantity of hydrocarbons since it would save considerable time and expense.

According to embodiments herein, the systems and methods in FIGS. 1-4 may be implemented entirely in terms of velocity ratio and measured compressional or shear sonic logs instead of in Vp-Vs space. The systems and methods of FIGS. 1-4 may be implemented by an acoustic logging tool, one or more processors connected to an acoustic logging tool, or a combination of both. Equations 7 and 8 can be cast in such a form as to allow either the P-wave or the S-wave velocity to be the dependent variable. Given below as equation 14 is an expression where the P-wave velocity is the dependent variable.

$$V_p = aV_s + C \qquad \text{Equation 14}$$

Where a is the slope and c the intercept of the regression trend.

Dividing both sides of equation 14 by S-wave velocity we obtain an expression in terms of velocity ratio and shear sonic travel time or slowness. Given below as equation 15.

$$\frac{V_p}{V_s} = b + d\Delta t_s \qquad \text{Equation 15}$$

Where once again, b and d are the intercept and slope respectively of the new equation. And $\Delta t_s$ is the shear sonic log. The velocity ratio can be determined by an acoustic logging tool, one or more processors connected to an acoustic logging tool, or a combination of both directly from the measured compressional and shear sonic logs by dividing the measured shear by the compressional sonic log. Equation 15 can be determined for both the fully brine-saturated and fully hydrocarbon-saturated trends and then used in the flow chart of FIG. 3 to estimate water saturation by an acoustic logging tool, one or more processors connected to an acoustic logging tool, or a combination of both.

To accentuate the separation between the fully brine trend and the fully hydrocarbon-saturated trend, especially in unconventional oil reservoirs, the model may also be implemented by an acoustic logging tool, one or more processors connected to an acoustic logging tool, or a combination of both entirely in terms of P-wave modulus (or bulk modulus) and shear modulus. The P-wave and shear modulus are both given by:

$$M = \rho * V_p^2 \qquad \text{Equation 17}$$

$$G = \rho * V_s^2 \qquad \text{Equation 18}$$

Where M is the P-wave modulus, G is the shear modulus, and $\rho$ is measured bulk density. P-wave modulus, bulk modulus and shear modulus are examples of elastic modulus.

As in the case of Vp and Vs, a regression trend relating G to M can also be determined.

$$G = aM + c \qquad \text{Equation 19}$$

Where a is the slope and c the intercept of the regression trend.

Equation 19 for the fully brine and fully hydrocarbon-saturated trend can also be determined as in equations 7 and 8 and used in the flow chart of FIG. 3 to determine water saturation. For example $a_0$ and $a_{100}$ may be a coefficient of M and $b_0$ and $b_{100}$ may be a coefficient of G. Equation 19 may be used the steps in FIG. 3 by an acoustic logging tool, one or more processors connected to an acoustic logging tool, or a combination of both.

Figure 8:
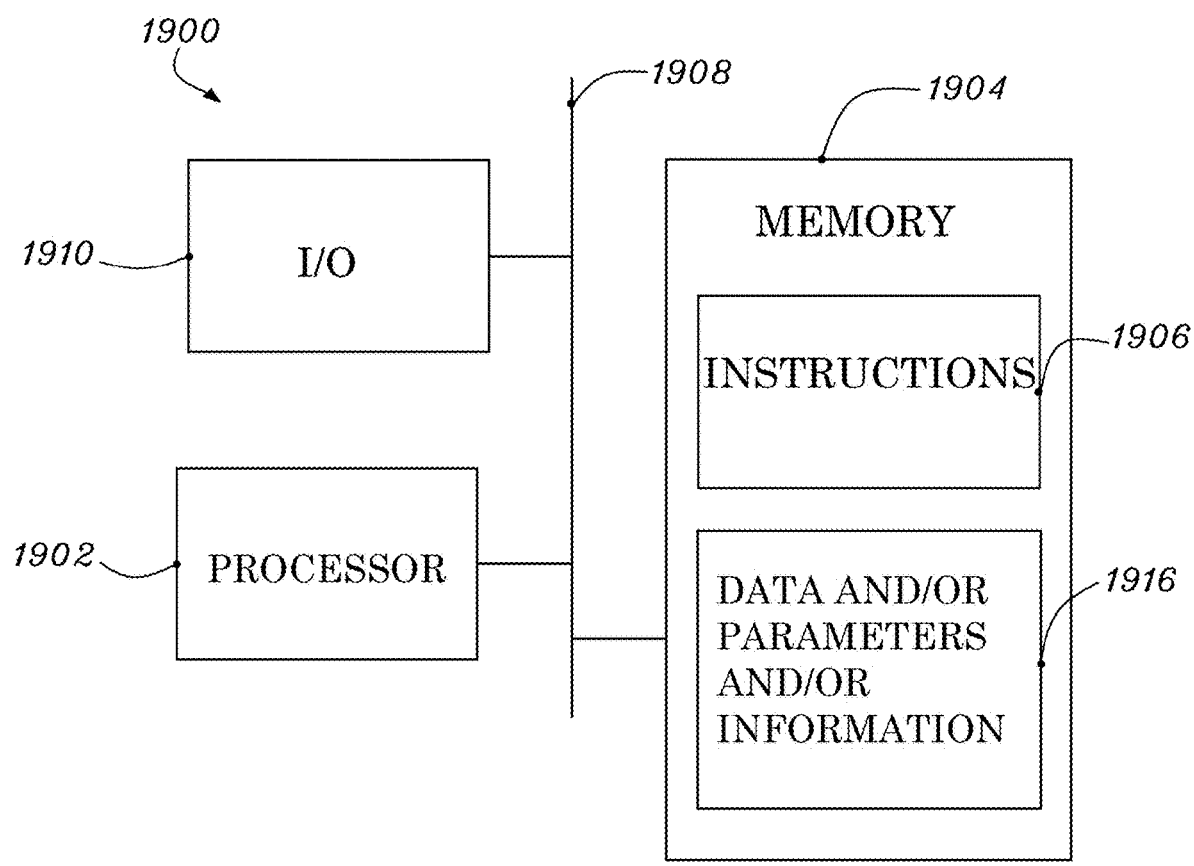
FIG. 8 is a high-level functional block diagram of a controller usable in conjunction with the system of FIGS. 1-7b, in accordance with an embodiment.

The embodiments included herein improve operation and determination of hydrocarbon saturation estimation over prior methods. The methods and systems included herein may be performed on one or more computer systems which may include one or more processors, memory, and interfaces for input and control. The methods and systems operate with a combination of hardware and software in order to carry out the steps described in the various embodiments. Instructions for carrying out method steps may be stored in a non-transitory computer readable medium. FIG. 8 depicts a high-level functional block diagram of a controller 1900 usable in conjunction with the embodiments herein. The controller 1900 includes input output 1910, processor 1902, and memory 1904. Input output 1910, processor 1902, and memory 1904 are connected by bus 1908. Memory 1904 includes instructions 1906 and other data 1916. Information in the form of electrical pulses is passed between the input output 1910, processor 1902, and memory 1904 to carry out the operation of controller 1900. Input output 1910 may be a display, touchscreen, mouse, keyboard, or a wired or wireless connection to another device. Instructions 1906 may include steps for carrying out functions or algorithms with processor 1902.

The invention claimed is:

1. A system of estimating hydrocarbon saturation of a hydrocarbon reservoir where at least an oil rig is operated to create a first wellbore into the hydrocarbon reservoir, the system comprising:
   an acoustic logging system, comprising:
      a motor and a cable, or a drill bit and at least one drilling pipe; and
      an acoustic measuring device positioned horizontally adjacent to the hydrocarbon reservoir within the first wellbore;
   a processor, wherein the processor is configured to:
      measure a compressional wave of a hydrocarbon-bearing interval within a first subsurface reservoir;
      measure a shear wave of the hydrocarbon-bearing interval across the first subsurface reservoir;
      determine a velocity of the compressional wave of the hydrocarbon-bearing interval;
      determine a velocity of the shear wave of the hydrocarbon-bearing interval;
      determine a fully brine-saturated trend for the hydrocarbon reservoir;
      determine a fully hydrocarbon-saturated trend for the hydrocarbon reservoir;
      determine a water saturation of the hydrocarbon reservoir based on a deviation of the velocity of the compressional wave of the hydrocarbon-bearing interval and the velocity of the shear wave of the hydrocarbon-bearing interval from the fully brine-saturated trend and the fully hydrocarbon-saturated trend; and estimate the hydrocarbon saturation of the hydrocarbon reservoir based on the determined water saturation, wherein the fully brine-saturated trend and the fully hydrocarbon-saturated trend are determined in terms of velocity ratio and shear sonic log or velocity ratio and compressional sonic log, wherein the determined water saturation is based on:

$$Swt = \frac{\frac{|a_0 x + b_0 y + c_0|}{\sqrt{a_0^2 + b_0^2}}}{\frac{|a_{100} x + b_{100} y + c_{100}|}{\sqrt{a_{100}^2 + b_{100}^2}}}$$

wherein $a_0$ is a coefficient of Vp/Vs where Vp is a velocity of a compressional wave and Vs is a shear wave velocity; $b_0$ is a coefficient of shear acoustic log (DTS), $c_0$ is an intercept of the fully hydrocarbon-saturated trend; $a_{100}$ is a coefficient of Vp/Vs where Vp is a velocity of a compressional wave and Vs is a shear wave velocity, $b_{100}$ is a coefficient of DTS, $c_{100}$ is an intercept of the fully brine-saturated trend, and Swt is a water saturation fraction of a total pore space at each lateral depth; or wherein $a_0$ is a coefficient of a bulk modulus (KB), $b_0$ is a coefficient of a shear modulus G, $c_0$ is the intercept of the fully hydrocarbon-saturated trend, $a_{100}$ is a coefficient of KB, $b_{100}$ is a coefficient of G; $c_{100}$ is the intercept of the fully brine-saturated trend, and Swt is water saturation fraction of a total pore space at each lateral depth; or wherein $a_0$ is a coefficient of Vp where Vp is a velocity of a compressional wave, $b_0$ is a coefficient of Vs where Vs is a shear wave velocity, $c_0$ is a coefficient of the fully hydrocarbon-saturated trend; $a_{100}$ is a coefficient of Vp where Vp is a velocity of a compressional wave, $b_{100}$ is a coefficient of Vs where Vs is a shear wave velocity, $c_{100}$ is a coefficient of the fully brine-saturated trend, and Swt is water saturation fraction of a total pore space at each lateral depth; or wherein $a_0$ is a coefficient of Vp/Vs where Vp is a velocity of a compressional wave and Vs is a shear wave velocity, $b_0$ is a coefficient of compressional acoustic log (DTC), $c_0$ is the intercept of the fully hydrocarbon-saturated trend, $a_{100}$ is a coefficient of Vp/Vs where Vp is a velocity of a compressional wave and Vs is a shear wave velocity, $b_{100}$ is a coefficient of DTC, $c_{100}$ is the intercept of the fully brine-saturated trend, and Swt is water saturation fraction of a total pore space at each lateral depth.

2. The system of claim 1, wherein the processor is further configured to:

measure a compressional wave of a water-bearing interval within the hydrocarbon reservoir; and measure a shear wave of the water-bearing interval across a second subsurface reservoir, wherein determining the fully brine-saturated trend is based on the measured compressional wave and the measured shear wave across the water-bearing interval of the second subsurface reservoir and determining the fully hydrocarbon-saturated trend is based at least in part on fluid substitution to 100% hydrocarbon saturation.

3. The system of claim 2, wherein the processor is further configured to determine the fully brine-saturated trend based on calibration to an empirical fully brine shale trend or an empirical fully brine sandstone trend.

4. The system of claim 3, wherein the calibration is based on one or more of:

$V_{s\_100} = 0.7697 * V_{p\_100} - 0.8673$ km/s, $V_{s\_100} = 0.527 * V_{p\_100} - 0.8673$ km/s, $V_{p\_0} = 5.41 - 6.35 * \phi - 2.87 * C$, and $V_{s\_0} = 3.57 - 4.57 * 0 - 1.83 * C$ wherein $V_{s\_100}$ is a shear velocity of the empirical fully brine shale trend, $V_{p\_100}$ is a compressional velocity of the empirical fully brine shale trend, $V_{s\_0}$ is an empirical shear velocity estimate of a fully dry shaly-sandstone, $V_{p\_0}$ is an empirical compressional velocity estimate of a fully dry shaly-sandstone C is clay volume, and $\phi$ is total porosity.

5. The system of claim 1, further comprising a display and instructions to display the hydrocarbon saturation for at least part of the hydrocarbon reservoir.

6. The system of claim 1, wherein the fully brine-saturated trend and the fully hydrocarbon-saturated trend are determined based on an elastic moduli computed from the measured compressional wave and the measured shear wave.

7. The system of claim 1, wherein the system is configured to be applied to a seismic volume to quantify hydrocarbon saturation in the first subsurface reservoir.

8. The system of claim 1, further comprising:

a first pipe to transport at least one hydrocarbon from the hydrocarbon reservoir utilizing equipment installed at the first wellbore.

9. The system of claim 1, further comprising, the estimated hydrocarbon saturation of the hydrocarbon reservoir as a fraction of the total pore space and is determined by:

hydrocarbon saturation=1−Swt.

10. The system of claim 1, wherein the motor is affixed to the oil rig.

11. The system of claim 1, wherein the acoustic measuring device transmits a first acoustic energy pulse and receives a second acoustic energy pulse.

12. A method of estimating hydrocarbon saturation of gas and oil reservoirs, the method comprising:

creating a wellbore in a hydrocarbon reservoir;

moving an acoustic measuring device to a position within the hydrocarbon reservoir;

measuring a compressional wave of a hydrocarbon-bearing interval within a first subsurface reservoir;

measuring a shear wave of the hydrocarbon-bearing interval across the first subsurface reservoir;

determining a velocity of the compressional wave of the hydrocarbon-bearing interval;

determining a velocity of the shear wave of the hydrocarbon-bearing interval;

determining a fully brine-saturated trend for the hydrocarbon reservoir;

determining a fully hydrocarbon-saturated trend for the hydrocarbon reservoir;

determining a water saturation of the hydrocarbon reservoir based on a deviation of the velocity of the compressional wave of the hydrocarbon-bearing interval and the velocity of the shear wave of the hydrocarbon-bearing interval from the fully brine-saturated trend and the fully hydrocarbon-saturated trend; and estimating the hydrocarbon saturation of the hydrocarbon reservoir based on the determined water saturation, wherein the fully brine-saturated trend and the fully hydrocarbon-saturated trend are determined in terms of velocity ratio and shear sonic log or velocity ratio and compressional sonic log, wherein the determined water saturation is based on:

$$Swt = \frac{\frac{|a_0 x + b_0 y + c_0|}{\sqrt{a_0^2 + b_0^2}}}{\frac{|a_{100} x + b_{100} y + c_{100}|}{\sqrt{a_{100}^2 + b_{100}^2}}}$$

wherein $a_0$ is a coefficient of Vp/Vs where Vp is a velocity of a compressional wave and Vs is a shear wave velocity; $b_0$ is a coefficient of shear acoustic log (DTS), $c_0$ is an intercept of the fully hydrocarbon-saturated trend; $a_{100}$ is a coefficient of Vp/Vs where Vp is a velocity of a compressional wave and Vs is a shear wave velocity, $b_{100}$ is a coefficient of DTS, $c_{100}$ is an intercept of the fully brine-saturated trend, and Swt is a water saturation fraction of a total pore space at each lateral depth; or wherein $a_0$ is a coefficient of a bulk modulus (KB), $b_0$ is a coefficient of a shear modulus G, $c_0$ is the intercept of the fully hydrocarbon-saturated trend, $a_{100}$ is a coefficient of KB, b100 is a coefficient of G; $c_{100}$ is the intercept of the fully brine-saturated trend, and Swt is water saturation fraction of a total pore space at each lateral depth; or wherein $a_0$ is a coefficient of Vp where Vp is a velocity of a compressional wave, $b_0$ is a coefficient of Vs where Vs is a shear wave velocity, $c_0$ is a coefficient of the fully hydrocarbon-saturated trend; $a_{100}$ is a coefficient of Vp where Vp is a velocity of a compressional wave, $b_{100}$ is a coefficient of Vs where Vs is a shear wave velocity, $c_{100}$ is a coefficient of the fully brine-saturated trend, and Swt is water saturation fraction of a total pore space at each lateral depth; or wherein $a_0$ is a coefficient of Vp/Vs where Vp is a velocity of a compressional wave and Vs is a shear wave velocity, $b_0$ is a coefficient of compressional acoustic log (DTC), $c_0$ is the intercept of the fully hydrocarbon-saturated trend, $a_{100}$ is a coefficient of Vp/Vs where Vp is a velocity of a compressional wave and Vs is a shear wave velocity, $b_{100}$ is a coefficient of DTC, $c_{100}$ is the intercept of the fully brine-saturated trend, and Swt is water saturation fraction of a total pore space at each lateral depth.

13. The method of claim 12, further comprising, inserting a first pipe into the hydrocarbon reservoir to transport at least one hydrocarbon; and
transporting the at least one hydrocarbon from the hydrocarbon reservoir.

14. The method of claim 12, further comprising, the estimated hydrocarbon saturation of the hydrocarbon reservoir is a hydrocarbon saturation percentage and is determined by:
Hydrocarbon saturation=1−Swt.

15. The method of claim 14, further comprising displaying the hydrocarbon saturation percentage for at least part of the hydrocarbon reservoir.

16. The method of claim 12, wherein the acoustic measuring device transmits a first acoustic energy pulse and receives a second acoustic energy pulse.

17. A non-transitory computer readable medium storing instructions that, when executed by a processor, cause the processor to perform operations comprising:
measure a compressional wave of a hydrocarbon-bearing interval within a first subsurface reservoir;
measure a shear wave of the hydrocarbon-bearing interval across a second subsurface reservoir;
determine a velocity of the compressional wave of the hydrocarbon-bearing interval;
determine a velocity of the shear wave of the hydrocarbon-bearing interval;
determine a fully brine-saturated trend for a hydrocarbon reservoir;
determine a fully hydrocarbon-saturated trend for the hydrocarbon reservoir;
determine a water saturation of the hydrocarbon reservoir based on a deviation of the velocity of the compressional wave of the hydrocarbon-bearing interval and the velocity of the shear wave of the hydrocarbon-bearing interval from the fully brine-saturated trend and the fully hydrocarbon-saturated trend; and
estimate a hydrocarbon saturation of the hydrocarbon reservoir based on the determined water saturation, wherein the fully brine-saturated trend and the fully hydrocarbon-saturated trend are determined in terms of velocity ratio and shear sonic log or velocity ratio and compressional sonic log, wherein the determined water saturation is based on:

$$Swt = \frac{\frac{|a_0 x + b_0 y + c_0|}{\sqrt{a_0^2 + b_0^2}}}{\frac{|a_{100} x + b_{100} y + c_{100}|}{\sqrt{a_{100}^2 + b_{100}^2}}}$$

wherein $a_0$ is a coefficient of Vp/Vs where Vp is a velocity of a compressional wave and Vs is a shear wave velocity; $b_0$ is a coefficient of shear acoustic log (DTS), $c_0$ is an intercept of the fully hydrocarbon-saturated trend; $a_{100}$ is a coefficient of Vp/Vs where Vp is a velocity of a compressional wave and Vs is a shear wave velocity, $b_{100}$ is a coefficient of DTS, $c_{100}$ is an intercept of the fully brine-saturated trend, and Swt is a water saturation fraction of a total pore space at each lateral depth; or wherein $a_0$ is a coefficient of a bulk modulus (KB), $b_0$ is a coefficient of a shear modulus G, $c_0$ is the intercept of the fully hydrocarbon-saturated trend, $a_{100}$ is a coefficient of KB, $b_{100}$ is a coefficient of G; $c_{100}$ is the intercept of the fully brine-saturated trend, and Swt is water saturation fraction of a total pore space at each lateral depth; or wherein $a_0$ is a coefficient of Vp where Vp is a velocity of a compressional wave, $b_0$ is a coefficient of Vs where Vs is a shear wave velocity, $c_0$ is a coefficient of the fully hydrocarbon-saturated trend; $a_{100}$ is a coefficient of Vp where Vp is a velocity of a compressional wave, $b_{100}$ is a coefficient of Vs where Vs is a shear wave velocity, $c_{100}$ is a coefficient of the fully brine-saturated trend, and Swt is water saturation fraction of a total pore space at each lateral depth; or wherein $a_0$ is a coefficient of Vp/Vs where Vp is a velocity of a compressional wave and Vs is a shear wave velocity, $b_0$ is a coefficient of compressional acoustic log (DTC), $c_0$ is the intercept of the fully hydrocarbon-saturated trend, $a_{100}$ is a coefficient of Vp/Vs where Vp is a velocity of a compressional wave and Vs is a shear wave velocity, $b_{100}$ is a coefficient of DTC, $c_{100}$ is the intercept of the fully brine-saturated trend, and Swt is water saturation fraction of a total pore space at each lateral depth.

* * * * *